(12) United States Patent
Chian

(10) Patent No.: US 7,790,459 B2
(45) Date of Patent: Sep. 7, 2010

US007790459B2

(54) IN VITRO MATURATION OF IMMATURE HUMAN OOCYTES

(75) Inventor: Ri-Cheng Chian, Longueuil (CA)

(73) Assignee: McGill University, Montreal, Quebec (CA)

( * ) Notice: Subject to any disclaimer, the term of this patent is extended or adjusted under 35 U.S.C. 154(b) by 0 days.

(21) Appl. No.: 11/969,522

(22) Filed: Jan. 4, 2008

(65) Prior Publication Data

US 2008/0176324 A1 Jul. 24, 2008

Related U.S. Application Data

(62) Division of application No. 10/506,713, filed as application No. PCT/CA2003/000323 on Mar. 7, 2003, now abandoned.

(60) Provisional application No. 60/362,395, filed on Mar. 8, 2002.

(51) Int. Cl.
*C12N 15/00* (2006.01)
(52) U.S. Cl. .................. 435/455; 435/29; 435/374
(58) Field of Classification Search .................. 435/455
See application file for complete search history.

(56) References Cited

U.S. PATENT DOCUMENTS

| 4,987,080 | A | 1/1991 | Grob et al. |
| 5,563,059 | A | 10/1996 | Alak et al. |
| 5,882,928 | A | 3/1999 | Moses |
| 6,211,429 | B1 | 4/2001 | Machaty et al. |
| 6,281,013 | B1 | 8/2001 | Grøndahl |
| 2001/0028878 | A1 | 10/2001 | Lindenberg et al. |
| 2002/0115211 | A1 | 8/2002 | Lindenberg et al. |

FOREIGN PATENT DOCUMENTS

| CA | 2199663 | 9/1998 |
| JP | 2000-1017160 | 1/2001 |
| SU | 1787034 | 1/1993 |
| WO | 90/13627 | 11/1990 |
| WO | 95/03817 | 2/1995 |
| WO | 99/67365 | 12/1999 |
| WO | 00/32140 | 6/2000 |
| WO | 00/50065 | 8/2000 |
| WO | 00/50066 | 8/2000 |
| WO | 01/38493 | 5/2001 |
| WO | 01/76360 | 10/2001 |

OTHER PUBLICATIONS

Eppig et al., Comparison of Embryonic Developmental Competence of mouse Oocytes with and without serum, Molecular Reproduction and development, vol. 32, p. 33-40, 1002.*
Hideo et al., Effect of growth factors in the medium for oocyte maturation and embryo culture on the development of in vitor matured and fertilized bovne oocytes, Japanese Journal of Embryo Transfer, vol. 21, 1999, Abstract.*
Caro et al., "Successful Fertilization, Embryo Development and Pregnancy in Human in Vitro Fertilization (IVF) using a chemically defined culture medium containing no protein", Journal of In vitro Fertilization and Embryo Transfer, vol. 3, No. 4, 215217 (1986).*
Child et al., "A Comparison of in vitro maturation and in vitro fertilization for women with polycystic ovaries," Obstetrics and Gynecology, 2002 p. 665-670.
Cobo et al., "Maturation in vitro of human oocytes from unstimulated cycles: selection of the optimal day for ovum retrieval based on follicular size," Human Reproduction, 1999, p. 1864-1868.
Brzyski, R.G. et al., "In Vitro Maturation of Oocytes Derived from Unstimulated Antral Follicles," *Assisted Reproduction*, 1999, 9(2), 79-86.
Downs, Stephen M. et al., "Induction of Maturation in Cumulus Cell-Enclosed Mouse Oocytes by Follicle-Stimulating Hormone and Epidermal Growth Factor: Evidence for a Positive Stimulus of Somatic Cell Origin," The Journal of Experimental Zoology, (1988), p. 86-96, vol. 245, Alan R. Liss, Inc.
Leese, Henry J. et al., "Production of Pyruvate by Isolate Mouse Cumulus Cells," The Journal of Experimental Zoology, (1995), p. 231-236, vol. 234, Alan R. Liss, Inc.
Adams, J., et al., "Prevalence of polycystic ovaries in women with anovulation and idiopathic hirsutism", (1986) Br. Med. J., vol. 293, p. 355-359.
Adamson, E.D., "Activities of growth factors in preimplantation embryos", (1993) J. Cell. Biochem, vol. 53, No. 4, p. 280-287.
Avery, B., et al. "Development of bovine oocytes, in vitro matured in a chemically defined protein-free medium, supplemented with different amino acid formulations", (1998) Theriogeneology, vol. 49, p. 306.
Bae, I.H., et al., "Utilization of glutamine for energy and protein synthesis by cultured rabbit follicular oocytes", (1975) Exptl. Cell. Res., vol. 90, p. 432-436.
Barnes, F.L., et al., "Blastocyst development and birth after in-vitro maturation of human primary oocytes, intracytoplasmic sperm injections and assisting hatching", (1995) Hum. Reprod., vol. 10, No. 12, p. 3243-3247.
Behbod, R., et al., "Will cancer stem cells provide new therapeutic targets?", (2004) Carcinogenesis, vol. 26, No. 4, p. 703-711.
Bevers, M.M., et al., "Regulation and modulation of oocyte maturation in the bovine", (1997) Theriogeneology, vol. 47, p. 13-22.
Biggers, J.D., et al., "The pattern of energy and metabolism in the mouse oocyte and zygote", (1967) Proc. Natl. Acad. Sci. USA, vol. 58, p. 560-567.
Blondin, P., et al, "Oocyte and follicular morphology as determining characteristics for developmental competence in bovine oocytes", (1995) Mol. Reprod. Dev., vol. 41, p. 54-62.
Brackett, B.G., et al., "Analysis of factors involved in the in vitro production of bovine embryos", (1993) Theriogeneology, vol. 39, p. 43-64.

(Continued)

*Primary Examiner*—Ralph Gitomer
*Assistant Examiner*—Tiffany M Gough
(74) *Attorney, Agent, or Firm*—Woodcock Washburn LLP

(57) ABSTRACT

The invention provides methods for in vitro maturation of immature human oocytes. In one aspect, the invention provides a method for in vitro maturation of immature human oocytes, comprising the steps of: (a) inducing in a female human subject an increase in endogenous luteinizing hormone levels, said subject having not undergone an ovarian stimulation protocol prior to said inducing step; (b) obtaining from said subject an immature oocyte; and (c) culturing said oocyte until maturity.

14 Claims, 5 Drawing Sheets

OTHER PUBLICATIONS

Braw-Tal, R., "Expression of mRNA for follisatatin and inhibin/activin subunits during follicular growth and astresia", (1994) J. Mol. Endocrinol., vol. 13, p. 253-264.

Brinster, R.L., "Radioactive carbon dioxide production from pyruvate and lactate by the preimplantation rabbit embryo", (1969) Exp. Cell. Res., vol. 54, p. 205-209.

Brinster, R.L., "Oxidation of pyruvate and glucose by oocytes of the mouse and rhesus monkey", (1971), J. Reprod. Fert., vol. 24, p. 187-191.

Cekleniak, N.A., et al., "A novel system for in vitro maturation of human oocytes", (2001) Fertil. Steril., vol. 75, No. 6, p. 1185-1193.

Cha, K.Y., et al., "Pregnancy after in vitro fertilization of human follicular oocytes collected from nonstimulated cycles, their culture in vitro and their transfer in a donor oocyte program", (1991) Fertil. Steril., vol. 55, No. 2, p. 109-113.

Cha, K.Y., et al., "Maturation in vitro of immature human oocytes for clinical use", (1998) Hum. Reprod. Update, vol. 4, No. 2, p. 103-120.

Chian, R.C., et al., "Effects of cumulus cells on male pronuclear formation and subsequent early development of bovine oocytes in vitro", (1994) Theriogeneology, vol. 41, p. 1499-1508.

Chian, R.C., et al., "Effects of cumulus cells and follicle-stimulating hormone during in vitro maturation on parthenogenetic activation of bovine oocytes", (1995) Mol. Reprod. Dev., vol. 42, p. 425-431.

Chian, RC., et al., "Molecular and structural characteristics between immature human oocytes retrieved from stimulated and unstimulated ovaries" (1997) Gomel V., et al. (eds.), The World Congress on in Vitro Fertilization and Assisted Reproduction; Monduzzi, Bologna, p. 315-319.

Chian, R.C., et al., "Pregnancies resulting from in vitro matured oocytes retrieved from patients with polycystic ovary syndrome after priming with human chorionic gonadotropin", (1999) Fertil. Sterl., vol. 72, p. 639-642.

Chian, R.C., et al., "Priming with human chorionic gonadotropin before retrieval of immature oocytes in women with infertility due to the polycystic ovary syndrome", (1999) New Eng. J. Med., vol. 341, p. 1624, 1626.

Chian, R.C., et al., "Production of steroids from human cumulus cells treated with different concentrations of gonadotropins during culture in vitro", (1999) Fertil. Steril., vol. 71, p. 61-66.

Chian, R.C., et al., "Prospective randomized study of human chorionic gonadotrophin priming before immature oocytes retrieval from unstimulated women with polycystic ovarian syndrome", .(2000) Hum. Reprod., vol. 15, No. I, p. 165-170.

Chian, R.C., et al., "Pregnancy and delivery after cryopreservation of zygotes produced by in-vitro matured oocytes retrieved from a woman with polycystic ovarian syndrome", (2001) Hum. Reprod., vol. 16, No. 8, p. 1700-1702.

Chian, R.C., et al., "Maturational and developmental competence of cumulus-free immature human oocytes derived from stimulated and intracytoplasmic sperm injection cycles", Reproductive BioMedicine Online, vol. 5, No. 2, p. 125-132, www.rbmonline.com/Article/696 on web Aug. 1.

Crosby, I.M., et al., "Follicle cell regulation of protein synthesis and developmental competence in sheep oocytes", (1981) J. Reprod. Fert., vol. 62, p. 575-582.

Cross, P.C., "The role of cumulus cells and serum in mouse oocyte maturation in vitro", (1973)1. Reprod. Fort, vol. 34, p. 241-245.

Cross, P.C., et al., "In vitro development of mouse oocytes", (1970) Biol. Reprod., vol. 3, p. 298-307.

De Vos, A., et al., "In-vitro matured metaphase-I oocytes have a lower fertilization rate but similar embryo quality as mature metaphase-II oocytes after intracytoplasmic sperm injection", (1999) Hum. Reprod., vol. 14, No. 7, p. 1859-1863.

Dekel, N., "Regulation of oocyte maturation. The role of cAMP", (1988) Ann. NY. Acad. Sci., vol. 541, p. 21.1-216.

Dimfeld, M., at al., "Functional differentiation in progesterone secretion by granulosa versus cumulus cells in the human preovulatory follicle and the effect of different induction of ovulation protocols", (1993) Fertil. Steril., vol. 60, No. 6, p. 1025-1030.

Donahue, R.P., et al., "Follicular cell support of oocyte maturation: production of pyruvate in vitro", (1968)3. Reprod. Fertil., vol. 17, p. 395-398.

Downs, S.M., et al., "The participation of energy substrates in the control of meiotic maturation in murine oocytes", (1994) Dev. Biol., vol. 162, p. 154-168.

Edirisinghe, W.R, et al., "Birth from cryopreserved embryos following in vitro maturation of oocytes and intracytoplasmic sperm injection", (1997) Hum. Reprod., vol. 12, No. 5, p. 1056-1058.

Eppig, J.J., et al., "Inhibition of oocyte maturation in mouse: participation of cAMP, steroid hormones, and a putative maturation-inhibitory factor", (1983) Dev. Biol., vol. 100, p. 39-49.

Fukui, Y., "Effect of follicle cells on the acrosome reaction, fertilization, and developmental competence of bovine oocytes matured in vitro", (1990) Mol. Reprod. Dev., vol. 26, p. 40-46.

Geshi, M., et al., "Effects of sodium pyruvate in nonserum maturation medium on maturation, fertilization, and subsequent development of bovine oocytes with or without cumulus cells", (2000) Biol. Reprod., vol. 63, p. 1730-1734.

Goldman, S., et al., "Different morphology and proliferative ability of cumulus and granulose cells originating from cystic follicles aspirated from stimulated in vitro fertilization patients", (1993) Fertil. Steril., vol. 59, No. 3, p. 601-605.

Goud, P.T., et al., "In-Vitro maturation of human germinal vesicle stage oocytes: role of cumulus cells and epidermal growth factor in the culture medium", (1998) Hum. Reprod., vol. 13, p. 1638-1644.

Gross-Weege, W., et al., "Inhibition of histamine release from rat peritoneal mast cells by a factor from human serum- identification as transferring", (1986) Hum. Reprod., vol. 19, p. 10-17.

Gwatkin, R.B.L., et al., "Requirements for the maturation of hamster oocytes in vitro", (1973) Exp. Cell. Res., vol. 76, p. 1-7.

Jaroudi, K.A., et al. "Embryo development and pregnancies from in vitro matured and fertilized human oocytes", (1999) Hum. Reprod., vol. 14, No. 7, p. 1749-1751.

Kane, M.T., et al., Peptide growth factors and reimplantation development, (1997) Hum. Reprod. Update, vol. 3,No. 2, p. 137-157.

Kennedy, J., et al., "Human Oocytes: Maturation in Chemically Defined Media", (1969) Science, vol. 164, p. 1292-1293.

Kim, H., et al., "Regulation of nuclear membrane assembly and maintenance during in vitro maturation of mouse oocytes: role of pyruvate and protein synthesis", (1991) Ca. Tissue Res., vol. 265, p. 105-112.

Laufer, N., et al., "Asynchrony between human cumulus-corona cell complex and oocyte maturation after human menopausal gonadotropin treatment for in vitro fertilization", (1984) Fertil. Steril., vol. 42, No. 3, p. 366-372.

Leese, H.J., et al., "Pyruvate and glucose uptake by mouse ova and preimplantation embryos". (1984) J. Reprod. Fen., vol. 72,p. 9-13.

Liu, J., et al., "Successful in vitro maturation of human oocytes not exposed to human chorionic gonadotropin during ovulation induction, resulting in pregnancy", (1997) Feirtil. Sterl., vol. 67, No. 3, p. 566-568.

MacDougall, M.J., et al, "A controlled study comparing patients with and without polycystic ovaries undergoing in-vitro fertilization", (1993) Hum. Reprod., vol. 8, No. 2, p. 233-237.

Malamitsi-Puchner., et al., "Concentrations of angiogenic factors in follicular fluid and oocyte-cumulus complex culture medium from women undergoing in vitro fertilization: Association with oocyte maturity and fertilization", (2001)Fertility and Sterility. vol. 76, No. 1, p. 98-101.

Maruo, T., et al., "Expression of epidermal growth factor and its receptor in the human ovary during follicular growth and regression", (1993) Endocrinology, vol. 132, No. 2, p. 924-931.

Moor, R.M., et al., "Hormonal and follicular factors affecting maturation of sheep oocytes in vitro and their subsequent developmental capacity", (1977)3. Reprod. Fert., vol. 49, p. 101-109.

Morgan, P.M., et al., "In vitro maturation of ovarian oocytes from unstimulated rhesus monkeys: assessment of cytoplasmic maturity by embryonic development after in vitro fertilization", (1991) Biol. Reprod., vol. 45, p. 89-93.

Nagy, Z.P., et al., "Pregnancy and birth after intracytoplasmic sperm Injection of in vitro matured germinal-vesicle stage oocytes: case report", (1996) Fertil. Steril., vol. 65, No. 5, p. 1047-1050.

Niwa, K., et al., "Fertilization of rat eggs in vitro at various times before and after ovulation with special reference to fertilization of ovarian oocyte matured in culture", (1975)3. Reprod. Fert, vol. 43, p. 435-451.

Patsoula, E., et at, "Expression of mRNA for the LH and FSH receptors in mouse oocytes and preimplantation embryos", (2001) Reproduction, vol. 121, p. 455-461.

Prins, G.S., et al., "Gonadotropins augment maturation and fertilization of human immature oocytes cultured in vitro", (1987) Fertil. Steril., vol. 47, No. 6, p. 1035-1037.

Rose, T.A., et al., "Effect of oocyte maturation medium on in vitro development of in vitro fertilized bovine embryos", (1992) Mol. Reprod. Dev., vol. 31, p. 72-77.

Schroeder, A.C., et al., "Factors affecting the developmental capacity of mouse oocytes undergoing maturation in vitro", (1988) Ann. NY. Acad. Sci., vol. 541, p. 197-204.

Schultz, R.M., et al., "Regulation of oocyte maturation in the mouse: possible roles of intercellular communication, cAMP and testosterone", (1983) Dev. Biol., vol. 95, p. 294-304.

Shea, B.F., et al., "Human follicular oocytes and their maturation in vitro", (1975) Fertil. Steril., vol. 26, No. II, p. 1075-1082.

Steptoe, J.D., et al., "Birth after the reimplantation of a human embryo", (1978) Lancet, ii :366.

Trouson, A., et al., "In vitro maturation and fertilization and developmental competence of oocytes recovered from untreated polycystic ovarian patients", (1994) Fertil. Steril., vol. 62, No. 2, p. 353-362.

Trouson, A., et al., "Oocyte maturation", (1998) Hum. Reprod., vol. 13, p. 52-62.

Trouson, A., et al., "Maturation of human oocytes in vitro and their developmental competence", (2001) Reproduction, vol. 121, p. 51-75.

Tucker, M.J., et al., "Birth after cryopreservation of immature oocytes with subsequent in vitro maturation", (1998) Fertil. & Steril., vol. 70, No. 3, p. 578-579.

Van Blerkom, J., et al., "Molecular differentiation of the rabbit ovum. II. During oocyte maturation in vivo and in vitro", (1978) Develop. Biol., vol. 63, p. 139-150.

Van Blerkom, J., et al., "Molecular differentiation of the rabbit ovum. LI. During the preimplantation development of in vivo and in vitro matured oocytes", (1978) Develop. Biol., vol. 63, p. 151-164.

Vanderhyden, B.C., et al., "Role of cumulus cells and serum on the in vitro maturation, fertilization, and subsequent development of rat oocytes", (1989) Biol. Reprod., vol. 40, p. 720-728.

Veeck. Ll, et al., "Maturation and fertilization of morphologically immature human oocytes in a program of in vitro fertilization", (1983) Fertil. Steril., vol. 39, No. 5, p. 594-602.

Warnes, G.M., et al., "Changes in protein synthesis during maturation of sheep oocytes in vivo and in vitro", (1977) J. Reprod. Fert., vol. 49, p. 331-335.

Watson R, et al., "Reverse transcription with nested polymerase chain reaction shows expression of basic fibroblast growth factor transcripts in human granulosa and cumulus cells from in vitro fertilization patients", (1992) Biochemical and Biophysical Research Communications, vol. 187, No. 3, p. 1227-1231.

Wynn, P., et al.., "Pretreatment with follicle stimulating hormone promotes the numbers of human oocytes reaching metaphase II by in-vitro maturation", (1998) Hum. Reprod., vol. 13, No. 11, p. 3132-3138.

* cited by examiner

IN VITRO MATURATION OF IMMATURE HUMAN OOCYTES

CROSS REFERENCE TO RELATED APPLICATIONS

This application is a Divisional of United States 371 National Phase application Ser. No. 10/506,713 filed May 17, 2005, which claims priority to PCT application number PCT/CA2003/000323 filed Mar. 7, 2003, which claims benefit of U.S. provisional application No. 60/362,395 filed on Mar. 8, 2002, the contents of which are incorporated herein by reference in their entirety.

FIELD

The present invention relates to the field of assisted reproductive technology (ART), particularly to methods for culturing immature human oocytes so that they mature to metaphase-II stage capable of being fertilized and forming a viable embryo.

BACKGROUND

Since the first successful human pregnancy by way of in vitro fertilization (IVF) was achieved in 1978, ART has helped thousands of thousands of women to overcome infertility problem Normally, during the follicular phase of a woman's reproductive cycle, only a single follicle grows to the preovulatory stage and releases its oocyte for potential fertilization. However, current IVF treatment requires that multiple oocytes be harvested. Therefore, women are normally pre-treated for approximately two or three weeks with gonadotropin releasing hormone agonists (GnRHa). After pituitary suppression has been achieved, human menopausal gonadotropin (HMG) or purified follicle-stimulating hormone (FSH) is administered to induce development of multiple follicles. Once two leading follicles have reached a diameter of at least about 18-20 mm, the patient is typically given 5,000 to 10,000 IU of human chorionic gonadotropin (HCG) to trigger final oocyte maturation. Approximately 36 hours later, a large number of oocytes (10 on average) are collected.

The harvested oocyte is then fertilized with the sperm. In many instances of human infertility, fertilization is effected by intracytoplasmic sperm injection (ICSI). Successful IVF generally requires that the oocyte have reached the metaphase-II (M-II) stage before fertilization is attempted. A M-II oocyte is ready to accept the sperm and be fertilized. Metaphase-II is characterized by exclusion of one polar body from the cytoplasm, and is typically detected by visual identification under a microscope.

The harvested oocyte remains surrounded by cumulus cells that support and promote the final maturation and development of the oocyte. The cumulus cells interfere with ICSI and obscure microscopic observation of the oocyte. Therefore, prior to ICSI, it is necessary to denude the oocyte of cumulus cells to permit determination of the level of oocyte maturity. This is generally accomplished by enzymatic and mechanical stripping of the cumulus cells.

Unfortunately, not all of the oocytes have matured to the M-II stage when they are harvested in ovarian stimulation. As a result of follicular asynchrony, in general, at least 10-15% of oocytes are still immature, and are at the germinal vesicle (GV) or metaphase-I (M-I) stage, at the time of harvest. These immature oocytes, denuded of cumulus cells, are discarded at most IVF clinics.

It would be desirable if these immature GV and M-I stage oocytes, presently wasted, could be brought to maturity, in vitro, and then successfully fertilized. Moreover, it would be desirable to be able to harvest immature oocytes from unstimulated ovaries and mature them to the M-II stage by way of in vitro maturation (IVM), thereby avoiding the entire regimen of treatment of women with GnRHa and stimulation of ovaries with gonadotropin. These procedures of ovarian stimulation require frequent blood sampling and ultrasound monitoring, at considerable cost. Moreover, current IVF treatment causes substantial discomfort and, in some cases, results in ovarian hyperstimulation syndrome (OHSS) and/or even death. There is also anxiety that the long-term effects of repeated ovarian stimulation may increase the risk of ovarian, endometrial and breast cancer.

Thus, there is substantial interest in developing IVF techniques that rely upon in vitro maturation of oocytes, rather than harvesting mature oocytes by ovarian stimulation. But only a few live births have been obtained from cumulus-denuded oocytes matured in vitro (Nagy et al., 1996; Jaroudi et al., 1997; Edirisinghe et al., 1997). Clearly then, there is an opportunity for improving the maturational and developmental competence of cumulus-denuded immature oocytes matured in vitro.

Recovery of immature oocytes followed by IVM of these immature oocytes is a potentially useful treatment for women with polycystic ovarian syndrome (PCOS) related infertility. PCOS is one of the most common reproductive disorders in women of childbearing age. It has a heterogeneous presentation, which is clinically characterized by anovulation and hyperandrogenism, and on pelvic ultrasound examination shows numerous antral follicles within the ovaries (Adams et al., 1986). There is a significantly higher risk of OHSS in these group of women compared with normal ovaries (MacDougall et al., 1993). Although the first pregnancy and live birth from immature oocytes retrieved from women with PCOS followed by IVM has been reported, the success rates are still low because oocyte maturation rates are relatively low.

Some attempts at developing IVM media and methods have involved the use of human follicular fluid, in an effort to mimic the conditions within the follicle. In view of the risk of transmission of disease, allergic reaction, etc., use of biological fluids in IVM techniques is prohibited in most countries. Instead, the use of a "chemically-defined medium", wherein the chemical composition of all of the ingredients is known, is preferred.

Mammalian immature oocytes removed from antral follicles will resume meiosis spontaneously without hormonal stimulation when cultured in a simple medium (Pincus & Enamann, 1935). However, oocyte maturation in vitro is profoundly affected by culture conditions.

Most attempts at human IVM have employed tissue culture medium 199 (TCM-199) as the maturation medium for immature oocytes (Trounson et al., 1994; Barnes et al., 1995; Chian et al., 1999a, 1999b, 2000, 2001). TCM-199 is a complex medium that contains many components, and was designed for in vitro culture of somatic cells, not germ cells. Notably, TCM-199 does not contain any growth factors. TCM-199 was first used for sheep oocyte IVM (Moor & Trounson, 1977), and has since been used routinely for bovine oocyte IVM (Brackett & Zuelke, 1993).

Although different culture media have been used to mature human oocytes (Shea et al., 1975; Cha et al., 1991; Trounson et al., 1994; Cha & Chian, 1998; Chian et al., 1999a, 1999b, 2000), it has been indicated recently that there is no apparent benefit for oocyte maturation, fertilization and embryonic development from use of these culture media (Trounson et al., 1998; 2001).

Thus, there remains a need for methods for maturing human oocytes in vitro.

SUMMARY

The present invention provides in vitro maturation methods that are useful for culturing immature human oocytes to maturity.

In a broad aspect, the invention provides a method for in vitro maturation of immature human oocytes, comprising the steps of:
(a) inducing in a female human subject an increase in endogenous luteinizing hormone levels, the subject having not undergone an ovarian stimulation protocol prior to the inducing step;
(b) obtaining from the subject an immature oocyte; and
(c) culturing the oocyte until maturity.

Preferably, prior to step (a), the subject has not been treated with a gonadotrophin releasing hormone agonist, human menopausal gonadotrophin, HCG, or follicle stimulating hormone (FSH).

In one embodiment, step (a) comprises administering to the subject HCG or luteinizing hormone (LH), or both. In a preferred embodiment, HCG is administered in an amount of about 5000 to about 20,000 IU, more preferably about 10,000 IU.

The immature human oocyte is preferably an M-I stage or GV stage ooctye. The oocyte preferably is cultured until it reaches M-II.

In one embodiment, the immature human oocyte is essentially free of cumulus cells and is cultured in a culture medium comprising:
at least one inorganic salt;
essential amino acids or a source thereof;
an energy source; and
at least one growth factor.

In one embodiment, the growth factor is fibroblast growth factor or epidermal growth factor, or both.

In one embodiment, the culture medium further comprises at least one hormone, e.g. insulin. In a preferred embodiment, the culture medium comprises from 0.5 mg/L to 50 mg/L insulin.

In one embodiment, the culture medium further comprises human transferrin, preferably from 5 mg/L to 500 mg/L human transferrin.

In one embodiment, the culture medium comprises from 0.0001 mg/L to 0.001 mg/L fibroblast growth factor.

In one embodiment, the culture medium comprises from 0.0001 to 0.01 mg/L epidermal growth factor.

In one embodiment, the culture medium comprises one or more vitamins, preferably biotin, D-Ca pantothenate, choline chloride, folic acid, i-inositol, nicotinamide, pyroxidal-HCl, riboflavin, and thiamine-HCl.

The culture medium may further comprise hydrocortisone or selenite, or both.

Preferred inorganic salts include $CaCl_2$, KCl, $MgSO_4$, NaCl, $NaHCO_3$ and $NaH_2PO_4 \cdot H_2O$.

Preferred energy sources include D-glucose and sodium pyruvate, or both D-glucose and sodium pyruvate.

In one embodiment, the amino acids comprise alanine, arginine, asparagine, aspartic acid, cystine, glutamic acid, glycine, histidine, isoleucine, leucine, lysine, methionine, phenylalanine, proline, serine, threonine, tryptophan, tyrosine, and valine.

In one embodiment, the culture medium comprises the inorganic salts, amino acids, vitamins and other components as set forth in Table 1, and wherein each inorganic salt, amino acid, vitamin and other component is present in an amount of ±50% (weight/volume), more preferably ±10% (weight/volume), of the amount specified in Table 1.

In another embodiment, the oocyte has a cumulus that is intact or at least partially intact, and/or the oocyte is cultured in the presence of cumulus cells.

In this embodiment, the oocyte may be cultured in a culture medium that is essentially free of one or more of epidermal growth factor, fibroblast growth factor, human transferrin, insulin, selenite, and hydrocortisone.

In one embodiment the oocyte is cultured in a culture medium comprising the inorganic salts, amino acids, vitamins and other components as set forth in Table 2, and wherein each inorganic salt, amino acid, vitamin and other component is present in an amount of ±50% (weight/volume), more preferably ±10% (weight/volume) of the amount specified in Table 2.

In one embodiment, the culture medium consists essentially of the inorganic salts, amino acids, vitamins and other components identified in Table 2.

In another embodiment, the culture medium consists of the inorganic salts, amino acids, vitamins and other components identified in Table 2.

In another embodiment, the invention provides a method for in vitro maturation of immature human oocytes, comprising culturing an immature human oocyte in a culture medium comprising:
at least one inorganic salt;
essential amino acids or a source thereof;
an energy source; and
at least one growth factor.

This embodiment is particularly useful when the immature human oocyte is essentially free of cumulus cells.

In another embodiment, the invention provides a method for in vitro maturation of immature human oocytes, comprising culturing an immature human oocyte in a culture medium comprising the inorganic salts, amino acids, vitamins and other components as set forth in Table 2. This embodiment is particularly useful when the immature human oocyte is cultured in the presence of cumulus cells.

In a preferred embodiment, the culture medium consists essentially of the inorganic salts, amino acids, vitamins and other components as set forth in Table 2.

In another preferred embodiment, the culture medium consists of the inorganic salts, amino acids, vitamins and other components as set forth in Table 2.

In particularly preferred embodiments, each inorganic salt, amino acid, vitamin and other component is present in an amount of ±50%, more preferably ±10% (weight/volume), of the amount specified in Table 2.

In another embodiment, certain of the components listed in the "other components" sections of Table 1 and 2 may be absent from the medium. Components that may be absent include, without limitation, phenol red, penicillin G, streptomycin, and human serum albumin. This may apply wherever reference is made herein to Table 1 or 2.

By the methods of the invention, increases may be obtained in one or more of:
(a) total number of oocytes reaching M-II stage;
(b) total number of oocytes fertilized;
(c) total number of embryos developing to the 8-cell stage; and
(d) total number of blastocysts formed;

as measured at 6 hours, 12 hours, 24 hours or 48 hours after commencement of maturation in IVM media in accordance with the invention. Increases in one or more of (a) to (d) of at least 10%, 20%, 30%, 40%, 50%, 60%, 70%, 80%, 90%, 100%, 200%, 300%, 400% or 500% may be advantageously obtained.

DETAILED DESCRIPTION OF ILLUSTRATIVE EMBODIMENTS

Candidates for IVM

Figure 1:
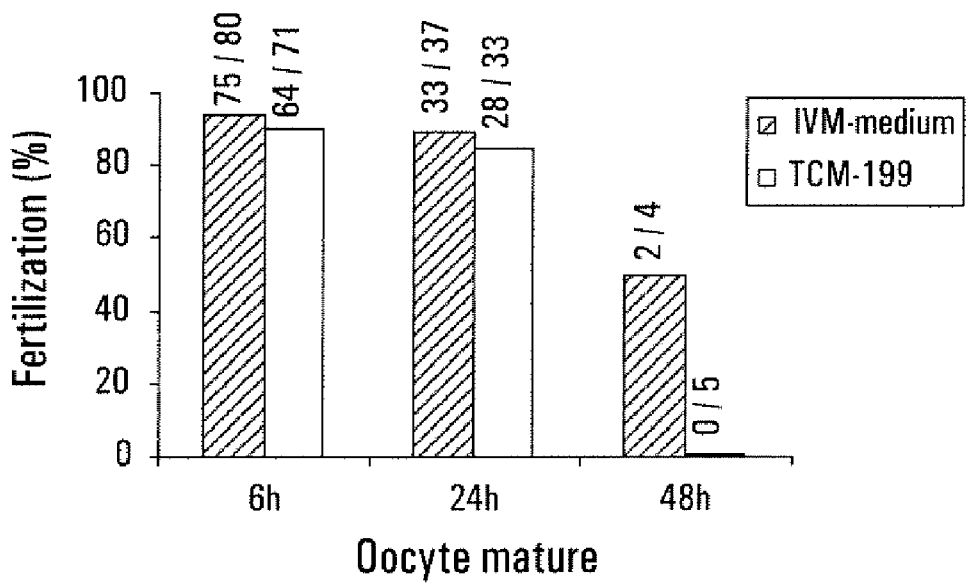
FIG. 1 shows fertilization rates of M-I stage oocytes derived from stimulation and ICSI cycles following 6 h, 24 h or 48 h of maturation, respectively.

Any female human subject who possesses viable oocytes is a candidate for IVM therapy. Typically, the subject will suffer from some form of infertility. For instance, the subject may experience normal oocyte production but have an impediment to fertilization, as in, e.g. PCOS or PCOS-like ovaries. IVM is also useful in women infertility with endometriosis, blockage of either or both fallopian tubes, etc. In typical PCOS, numerous follicles mature simultaneously in the ovaries, without the appearance of a dominant follicle. The subject's menstrual cycle may be regular, irregular or non-existent. IVM may be especially useful in women who are susceptible to or suffer from OHSS and are therefore not suitable candidates for traditional in vitro fertilization techniques involving an ovarian stimulation protocol.

Alternatively, the subject may be an individual who does not suffer from infertility or have any reproductive impediment whatsoever, but for whom an in vitro fertilization method nevertheless remains desirable, as in, e.g. cases of male factor infertility.

Absence of Ovarian Stimulation Protocol

Unlike in conventional in vitro fertilization methods, IVM in accordance with the invention does not necessarily involve an ovarian stimulation protocol. One of two "ovarian stimulation protocols" is usually used in conventional IVF, a "long protocol" or a "short protocol." The long protocol has two steps. The first step involves pre-treating the subject for two or three weeks with GnRHa to down-regulate pituitary activity. Once pituitary suppression has been achieved, in the second step, HMG or FSH is administered to induce the development of multiple follicles. The short protocol involves only the ovarian stimulation step, but not the down-regulation step.

Ovarian stimulation is required in conventional IVF techniques to permit the oocytes to mature to the M-II stage prior to harvest. In the present invention, wherein oocytes are harvested at an immature stage, i.e. prior to reaching the M-II stage, ovarian stimulation need not be used. That is, the subject need not be pre-treated with GnRHa's, HMG and/or FSH.

Increasing Endogenous Levels of Luteinizing Hormone (LH)

Prior to retrieving immature oocytes, an increase in endogenous levels of LH is induced in the subject (also described herein as "priming"). This may be accomplished by e.g. administering to the subject an effective amount of human chorionic gonadotropin (HCG) (Profasi Serono, Oakville, Ontario, Canada) or LH, either of which stimulate endogenous LH production. Baseline concentration of LH in the plasma of premenopausal women is usually about 2-4 mIU/ml, and at midcycle peak may be up to 25-35 mIU/ml. The expression "inducing in a female human subject an increase in endogenous luteinizing hormone levels" means increasing the plasma LH concentration above the baseline concentration. Preferably plasma LH concentration is increased at least 100%, 200%, 300%, 400%, 500%, 600%, 700%, 800%, 900%, 1000%, or 2000% above baseline concentration.

The dosage and mode of administration of HCG or LH may vary depending on the patient and the circumstances and may be determined by those of skill in the art. Subcutaneous injection is a preferred mode of administration although other modes of administration may be used. A single injection of about 5000 to about 20,000 IU of HCG is generally sufficient, with a single dose of about 10,000 IU of HCG being preferred.

In the case of a subject having a regular menstrual cycle, the time for inducement may be determined relative to the commencement of menstrual bleeding, which is considered "day 0". In a subject having an irregular or absent menstrual cycle, commencement of menstrual bleeding (i.e. the initiation of "day 0") can be achieved by procedures known in the art, e.g. by the administration of progesterone (available from e.g. Prometrium; Schering, Pointe-Claire, Quebec, Canada), e.g. intravaginally, in an amount of approximately 300 mg/day for 10 days.

Typically, on day three and day eight, the ovaries are examined by ultrasound to assess the size and the number of follicles. Usually, the dominant follicle reaches a diameter of at least about 16 mm by day 10-14.

In instances where a dominant follicle is present (e.g. as in normal ovarian function, as in the case of a healthy subject or a subject suffering from e.g. endometriosis or tubal blockage) the increase in endogenous LH activity is induced (e.g. by administration of HCG) when the dominant follicle reaches a diameter of about 15-17 mm, preferably at least about 16 mm.

If a dominant follicle is not present, as in cases of e.g. PCOS, inducement of an increase in endogenous LH levels preferably occurs when the follicles are less than about 12 mm in diameter.

Retrieval of Immature Oocytes

Oocytes are generally retrieved from about 32 to about 40 hours after priming, more preferably about 34 to 38 hours after priming and even more preferably about 36 hours after priming. Means for retrieving oocytes are known in the art. In one embodiment, transvaginal ultrasonographically-guided oocyte collection is done using a 17-20 gauge, preferably 19 gauge single-lumen aspiration needle at an aspiration pressure of from about 5 to about 10 kPa, preferably about 7.5 kPa.

Culture of Immature Oocytes

As used herein, the term "immature human oocyte" means a human oocyte that has not yet reached metaphase-II (M-II). As discussed previously, metaphase-II is characterized by exclusion of one polar body from the cytoplasm. Immature human oocytes used in the invention are typically at the germinal vesicle (GV) or metaphase-I (M-I) stage.

Oocytes may be cultured with their cumulus intact, in a form known as a "cumulus-oocyte-complex" (COC), or oocytes may be partially or entirely denuded from cumulus cells. COC can be stripped with 85 IU/ml hyaluronidase in HEPES buffered medium and mechanically pipetted until oocytes are denuded. An oocyte that is "essentially free of cumulus cells" is an oocyte that is associated with sufficiently few cumulus cells that the cumulus cells have no detectable physiological effect on the oocyte.

Culture conditions for human oocytes are known in the art and are not critical to the invention. Suitable culture conditions include e.g. culturing the oocytes at 37° C. in an atmosphere of 95% air and 5% $CO_2$ at high humidity, e.g. 100% humidity. A "triple gas" atmosphere of 5% $O_2$, 5% $CO_2$ and 90% $N_2$ may also be used. Mineral oil may be overlaid on the medium to control evaporation and/or temperature. Oocytes are typically cultured in a well containing 1 ml of culture medium or more, or may be cultured in 10 μl of culture medium or less in a droplet in a culture dish.

Immature oocytes may be cultured for e.g. about 24 to about 48 hours. Because about 60% of oocytes typically reach maturity (M-II) after 24 hours of culture, when oocytes are cultured with an intact or partially intact cumulus, they may be denuded at about 24 hours and observed under a microscope to assess oocyte maturity. The physiological influence of the cumulus cells on the oocyte persists for only about the first 12 hours in culture, so denuding the oocyte after about 24 hours in culture has little or no negative effect.

Culture Medium for Oocytes Essentially Free of Cumulus Cells

Due to the influence of cumulus cells on the maturation of oocytes, somewhat different culture media may be used when the oocytes are cultured for the first 12-24 hours in the presence of cumulus cells. This can occur e.g. when the oocytes are cultured as COCs or partially denuded or when denuded oocytes are co-cultured in the presence of cumulus cells.

The inorganic salts, essential and non-essential amino acids, and energy source in the IVM medium are not critical to the invention. Suitable salts, amino acids and energy sources are known in the art.

Inorganic salts are provided to buffer the pH of the medium within a range preferably of about 7.2-7.4 and to maintain correct osmolarity of the medium with the oocytes. Suitable inorganic salts and concentrations thereof as used in culture media are known in the art. Typical inorganic salts include $CaCl_2$, KCl, $MgSO_4$, NaCl, $NaHCO_3$, $NaH_2PO_4.H_2O$, $FE(NO_3)_3.9H_2O$, $KH_2PO_4$, Na acetate, $Na_2H_2PO_4$, etc.

The IVM medium contains at least one amino acid or source thereof. Preferably, at least the essential amino acids, or sources thereof, are included in IVM medium. "Essential" amino acids are those amino acids not synthesized in the oocyte and that are essential for protein synthesis. The essential amino acids are generally considered to be isoleucine, leucine, lysine, methionine, phenylalanine, threonine, tryptophan and valine. A commercial amino acid mixture, containing the eight essential amino acids as well as some or all of the remaining non-essential amino acids may conveniently be used. Non-naturally occurring amino acids or amino acid derivatives as are known in the art may also be included in the IVM medium. In a particularly preferred embodiment, the IVM medium of the invention comprises alanine, arginine, asparagine, aspartic acid, cystine, glutamic acid, glutamine, glycine, histidine, isoleucine, leucine, lysine, methionine, phenylalanine, proline, serine, threonine, tryptophan, tyrosine, and valine.

The IVM medium preferably contains vitamins as are known in the art for inclusion in culture media. Vitamins that may be included in the media include, without limitation, vitamins A1 (retinol), A2 (an alternative form of retinol), B1 (thiamine), B2 (riboflavin), B6 (pyridoxine), B9 (folic acid), B12 (cyanocobalamin), B17, C (ascorbic acid), D, D2 (calciferol), D3 (cholecalciferol), E (tocopherol), H (biotin), K, K1 (phylloquinone), K2, K3 (menadione), P, etc. A particularly preferred combination of vitamins comprises biotin, D-Ca pantothenate, choline chloride, folic acid, i-inositol, nicotinamide, pyroxidal-HCl, riboflavin, and thiamine-HCl.

The IVM medium contains at least one growth factor (GF). Broadly speaking, growth factors are proteins that bind to receptors on the cell surface, with the primary result of activating cellular proliferation and/or differentiation. Many growth factors are quite versatile, stimulating cellular division in numerous different cell types, while others are specific to a particular cell-type. Growth factors may act on membranes of oocytes to positively stimulate oocyte maturation (Maruo et al., 1993; Goud et al., 1998). Useful growth factors in the context of the present invention include those selected from the following growth factor superfamilies: epidermal growth factor (EGF) family; platelet derived growth factor (PDGF) family; insulin-like growth factor (IGF) family; nerve growth factor (NGF) family; transforming growth factor (TGF) family; fibroblast growth factor (FGF) family; hepatocyte growth factor (HGF) family; hemapoietic growth factors; and cytokines.

In a preferred embodiment, the growth factors in IVM medium comprise fibroblast growth factor (FGF) and epidermal growth factor (EGF). FGF and EGF are readily available from commercial sources, and may be purchased together in a cell growth supplement. The IVM medium preferably contains from 0.0001 mg/L to 0.001 mg/L FGF, more preferably from 0.0002 mg/L to 0.001 mg/L FGF, and even more preferably about 0.0005 mg/L FGF. The IVM medium preferably contains from 0.0001 to 0.01 mg/L EGF, more preferably from 0.0005 mg/L to 0.002 mg/L EGF, and even more preferably about 0.001 mg/L EGF.

The IVM medium preferably also contains at least one hormone. Preferred hormones include insulin, estradiol, follicle-stimulating hormone (FSH) and luteinizing hormone (LH). Human menopausal gonadotropin (HMG) can generally be substituted for FSH, and human chorionic gonadotropin (HCG) can generally be substituted for LH. In a preferred embodiment, the IVM medium comprises insulin. Normally, insulin is involved in energy metabolism and amino acid transportation into cells. The IVM medium preferably contains from 0.5 mg/L to 50 mg/L insulin, more preferably 0.25 mg/L to 10 mg/L insulin, and even more preferably about 5 mg/L insulin. In a particularly preferred embodiment, the IVM medium further comprises estradiol, LH and FSH. The amount of estradiol is preferably about 1 μg/ml±10%,±20%, ±30%, ±40% or ±50%. The amount of each of FSH and LH is preferably about 0.08 IU/ml±10%, ±20%, ±30%, ±40% or ±50%.

In a preferred embodiment, the IVM medium also contains human transferrin (TF). TF is a 75 kDa glycoprotein containing 679 amino acids and two glycan chains. For each, the last residue is a sialic (N-acetyl neuraminic) acid, which can be hydrolyzed by neuraminidase. TF not only transports iron in all extracellular fluid but also exerts many additional properties, including cell growth stimulation (Gross-Weege et al., 1986). The IVM medium preferably contains from 5 mg/L to 500 mg/L TF, more preferably from 25 mg/L to 100 mg/L TF, and even more preferably about 50 mg/L TF.

The growth factors, hormones and transferrins discussed above may be naturally occurring, synthetic or recombinant, and encompass biologically active fragments, variants, derivatives and homologs of these substances that retain at least some of the biological activity of the naturally-occurring, synthetic or recombinantly-produced substances. By way of a non-limiting example, a protein may include one or more amino acid insertions, deletions, substitutions or modifications without substantially reducing its biological activity.

The choice of energy source is not critical to the invention, and may be e.g. glucose, sodium pyruvate, lactate, or a mixture of some or all of these energy sources.

The IVM medium may additional contain additional components such as selenite or selenium and hydrocortisone.

Buffers for controlling the pH of the medium may be added, such as Hepes, as may be pH indicators such as phenol red.

Antibiotics such as penicillin G and streptomycin may be added to the IVM medium to prevent contamination.

Synthetic Serum Supplement (SSS) may be included in the IVM medium as a source of protein for the oocyte and to prevent cells from adhering to glassware during in vitro culture. SSS has the advantage of having received regulatory approval for human IVF, and is commercially available.

In a particularly preferred embodiment, the IVM medium includes the components set forth in Table 1. The absolute and relative quantities of each component can vary substantially, for example by up to ±10%, ±20%, ±30%, ±40%, ±50% weight by volume.

Culture Medium for Oocytes in the Presence of Cumulus Cells

Culture media as described above are also useful for culturing immature oocytes that have a cumulus that is intact or at least partially intact, and/or that are co-cultured with cumulus cells. But the presence of the cumulus cells in the first 12-24 hours of culture eliminates the need for growth factors, so the culture medium need not contain growth factors such as fibroblast growth factor, epidermal growth factor, etc.

Also, whereas the culture medium described in the preceding section preferably contains human transferrin, insulin, selenite and hydrocortisone, these are not of substantial benefit when culturing oocytes in the presence of cumulus cells, and are therefore generally absent from the culture medium.

More generally, complex culture media, such as tissue culture media (e.g. TCM-199), contain many components that are designed specifically for somatic cell culture in vitro rather than for oocyte culture. The use of complex culture media such as TCM-199 provides poorer results than if less complex media as described herein are used. Thus, in particularly preferred embodiments, oocytes that are essentially free of cumulus cells are cultured in media that consists of, or consists essentially of the components listed in Table 1; and oocytes that are cultured in the presence of cumulus cells are cultured in media that consists of or consists essentially of the components listed in Table 2.

The term "comprising" is intended to be inclusive or open-ended and does not exclude additional, unrecited elements or method steps. The term "consisting of" is intended to exclude any element, step, or ingredient that is not specified, but for impurities ordinarily associated with specified ingredients or materials. The term "consisting essentially of" is intended to occupy a middle ground between "comprising" and "consisting of" and to exclude other than the specified materials or steps and those that do not materially affect the basic and novel characteristics of the invention herein.

Fertilization of Oocytes and Culture of Embryos

Techniques for fertilizing oocytes and culturing embryos are known in the art.

In one embodiment, fertilization is accomplished by intracytoplasmic sperm injection (ICSI). Generally, spermatozoa can be prepared by gradient separation by centrifugation or by "swim-up" followed by washing with a suitable medium such as HTF supplemented with 10% SSS. A single spermatozoon may be injected into an M-II oocyte. Following ICSI, the oocyte may be transferred to e.g. fertilization medium supplemented with 10% SSS in a tissue culture dish. Fertilization can be detected by the appearance of two distinct pronuclei and two polar bodies approximately 16-18 hours after ICSI.

In one embodiment, fertilized oocytes may be cultured in fertilization media until about 72 hours after ICSI and then transferred to e.g. embryo developmental medium (Vitrolife, Göteborg, Sweden) in a tissue culture dish under mineral oil for an additional 48 hours.

As used herein, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The invention is further illustrated by reference to the following non-limiting examples.

EXAMPLE 1

Source of Immature Oocytes

A total of 521 immature oocytes (213 oocytes at GV stage and 308 oocytes at M-I stage) were collected from 183 women (age range between 28 to 40 years) who underwent controlled ovarian stimulation and ICSI cycles under informed consent. Ovarian stimulation was performed with GnRHa, HMG or FSH and HCG using standard protocols.

36 hours after HCG injection, oocyte retrieval was carried out using an ultrasound-guided trans-vaginal probe. The collected COC were cultured in human tubal fluid medium (HTF; Irvine Scientific) supplemented with 10% synthetic serum substitute (SSS; Irvine Scientific) and placed in a 5% $CO_2$ incubator (37° C. with high humidity) for at least 1 h before they were stripped from their cumulus cells.

COC were stripped with 85 IU/ml hyaluronidase in HTF medium and mechanical pipetting. All oocytes were completely denuded from their cumulus cells. Denuded oocytes were observed under an inverted microscope to assess for oocyte maturity. The mature oocytes were determined by the presence of a first polar body extrusion (1PB). The oocytes with a visual polar body (M-II) were provided for clinical application to perform the ICSI procedure immediately. Immature oocytes were defined by the absence of 1PB and then identified as GV or M-I stages depending upon whether the oocytes contained a visible GV in the cytoplasm under microscope. Immature oocytes without a GV in the cytoplasm were considered as M-I stage. These immature oocytes were used for in vitro maturation.

The immature oocytes were cultured in HTF medium supplemented with 10% SSS (Irvine Scientific) placed in a 37° C. and 5% CO$_2$ incubator before transferred to the maturation medium. The time of the immature oocytes were transferred to maturation medium is defined as the starting point for maturation in culture. Normally, it takes approximately 3-4 h from oocyte retrieval to the start of oocyte maturation.

In Vitro Maturation of the Immature Oocytes

Immature oocytes were divided into two groups. One was the GV stage oocytes (n=213), another was the M-I stage oocytes (n=308). Each group of oocytes was randomly cultured in one of two maturation media respectively: (1) TCM-199 (GIBCO, Catalogue No. 11153) or, (2) IVM-medium (Table 1). Both TCM-199 and IVM-medium were supplemented with 10% SSS (Irvine Scientific), 0.075 IU/ml FSH+LH (Humegon, Ontario, Canada) and, 1.0 μg/ml estradiol (Sigma). Additional supplements to TCM-199 included 0.25 mM sodium pyruvate (Sigma), 0.05 unit/ml penicillin G and streptomycin (GIBCO).

Before culture, the immature oocytes were washed at least twice in maturation medium. The immature oocytes were cultured in an organ tissue culture dish (60×15 mm; Falcon) containing 1 ml of maturation medium (TCM-199 or IVM-medium) at 37° C. in an atmosphere of 5% CO$_2$ and 95% air with high humidity. A maximum of 5 oocytes (1 to 5) were placed in each organ tissue culture dish.

Following culture, the maturity of the oocytes was determined under the microscope at 6 h for M-I stage oocytes and then at 24 h and 48 h for both M-I and GV stage oocytes.

Intracytoplasmic Sperm Injection (ICSI)

In vitro matured oocytes were inseminated by ICSI with sperm of the patient's husband. All semen samples were obtained from the ejaculate for clinical utilization. The remaining samples were donated for this experiment under informed consent.

Sperm for ICSI were prepared by PureSperm (Nidacon, Sweden) gradient separation (45%, 70% and 90%) at 560 g for 20 min. Following gradient separation, the sperm pellet was washed twice (200 g) with 2 ml of HTF medium (Irvine Scientific) supplemented with 10% SSS.

A single sperm was injected into each M-II oocyte. Following ICSI, each oocyte was transferred into a 20 μl droplet of HTF medium supplemented with 10% SSS in a tissue culture dish (35×10 mm; Falcon) under mineral oil (Sigma).

Fertilization was assessed 16-18 h after ICSI for the appearance of two distinct pronuclei and two polar bodies. Since the oocytes were not matured at the same time following culture, the sperm samples were kept in 5 ml Falcon tubes (tight tube cap) containing 0.5-1.0 ml HTF medium supplemented with 10% SSS at room temperature for further insemination by ICSI at 6 h, 24 h or 48 h, respectively.

Culture of Embryos

Fertilized oocytes (with two pronuclei) were cultured in HTF medium supplemented with 10% SSS until 72 h after ICSI, and then each embryo was transferred into a 20 μl droplet of G2.2 medium (VitroLife, Sweden) in a tissue culture dish (35×10 mm; Falcon) under mineral oil (Sigma) further culture for 48 h. Embryo development was recorded at 24 h intervals following culture until day 5 (120 h). All embryos were destroyed on day 5 following consent instruction from the patients.

Statistical Analysis

Statistical significant differences in the percentages of oocyte maturation, fertilization and development between the groups were determined and compared by Student-Newman-Keuls' test (Steel & Torrie, 1980). A P—value of <0.05 was considered statistically significant.

Results

As shown in Table 3, 52.0% and 46.1% of M-I stage oocytes were mature 6 h after culture in the IVM medium and TCM-199, respectively. Following further culture for 24 h and 48 h, there were no differences in oocyte maturation rates between IVM-medium (76.0% and 78.6%) and TCM-199 (67.5% and 70.8%).

As shown in Table 4, the final fertilization rates also were not different between these two media (90.0% vs. 84.4%).

FIG. 1 shows the fertilization rates of the oocytes matured in the IVM-medium or TCM-199 at 6 h (93.8% vs. 90.1%), 24 h (89.2% vs. 84.9%) and 48 h (50.0% vs. 0.0%), respectively.

Figure 2:
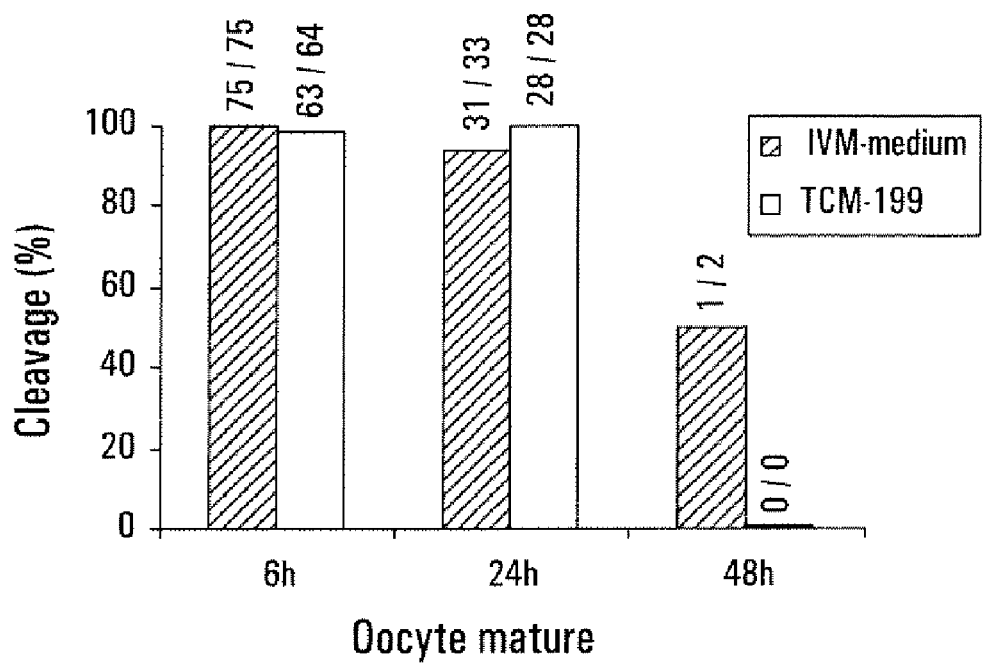
FIG. 2 shows cleavage rates of M-I stage oocytes derived from stimulation and ICSI cycles following 6 h, 24 h or 48 h of maturation, respectively.

The final cleavage rates of the fertilized oocytes were not different between the oocytes matured in these two media (Table 4; 97.3% vs. 98.9%), and there were also no differences in these two media when the oocytes were matured 6 h (100.0% vs. 98.4%) and 24 h (93.9% vs. 100.0%) respectively (FIG. 2).

Figure 3A:
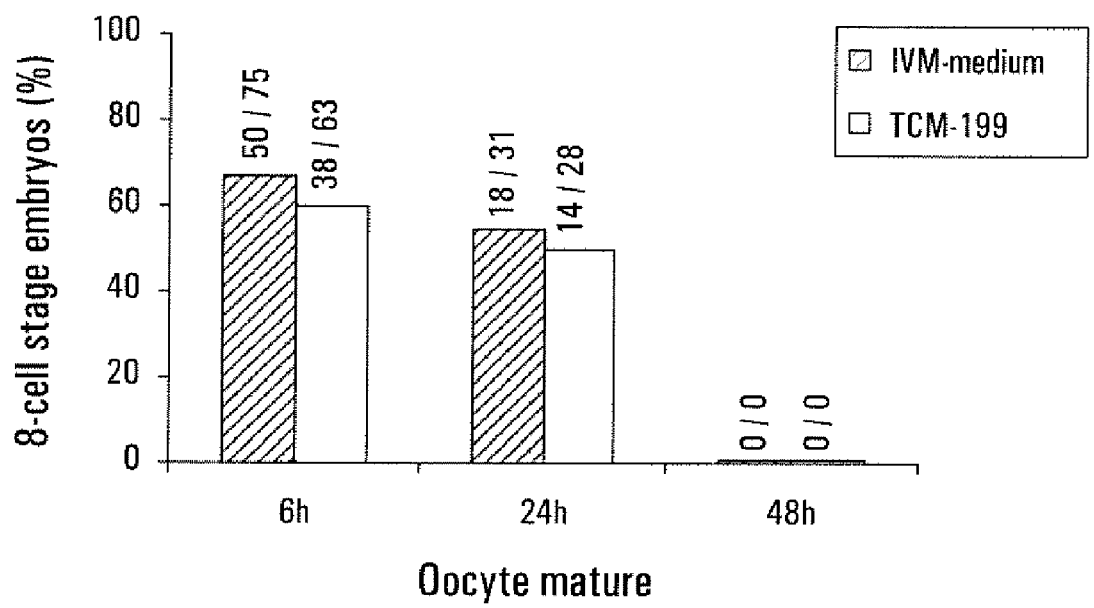
FIGS. 3A and 3B show embryos developing to the 8-cell stage (A) and the blastocyst stage (B) following 6 h, 24 h or 48 h of maturation of M-I stage oocytes derived from stimulation and ICSI cycles.

There were no significant differences in the embryos that developed to the 8-cell stage between the oocytes matured in IVM-medium (63.7%) and TCM-199 (57.1%), and the percentages of embryos that developed to the 8-cell stage were also not different when the oocytes matured 6 h (66.7% vs. 60.3%), 24 h (54.6% vs. 50.0%) and 48 h (0.0% vs. 0.0%) in these two media, respectively (FIG. 3a).

Figure 3B:
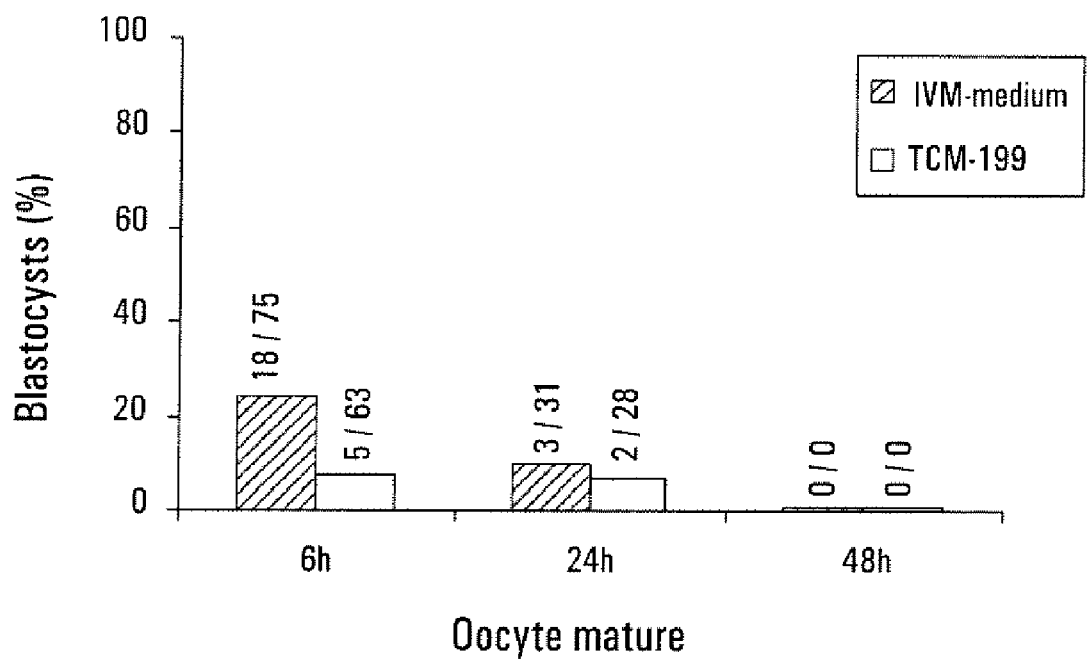

However, total blastocyst formation rates were significantly different (P<0.05) between the IVM-medium and TC-199 respectively (Table 4; 19.6% vs. 7.7%). Furthermore, the percentage of blastocyst formation was different (P<0.05) for these two media when the oocytes matured 6 h (24.0% vs. 7.9%) after maturation in culture (FIG. 3b).

However, there were no differences between these two media when the oocytes matured 24 h (9.7% vs. 7.1%) and 48 h (0.0% vs. 0.0%), respectively. As shown in Table 5, when GV stage oocytes were matured in vitro, there were significant differences (P<0.01) in the maturation rates between the IVM-medium and TCM-199 at 24 h (50.1% vs. 34.0%) and 48 h (75.7% vs. 55.7%) respectively.

However, as shown in Table 6, the final fertilization rates were not different between the IVM-medium (86.4%) and TCM-199 (78.0%).

Figure 4:
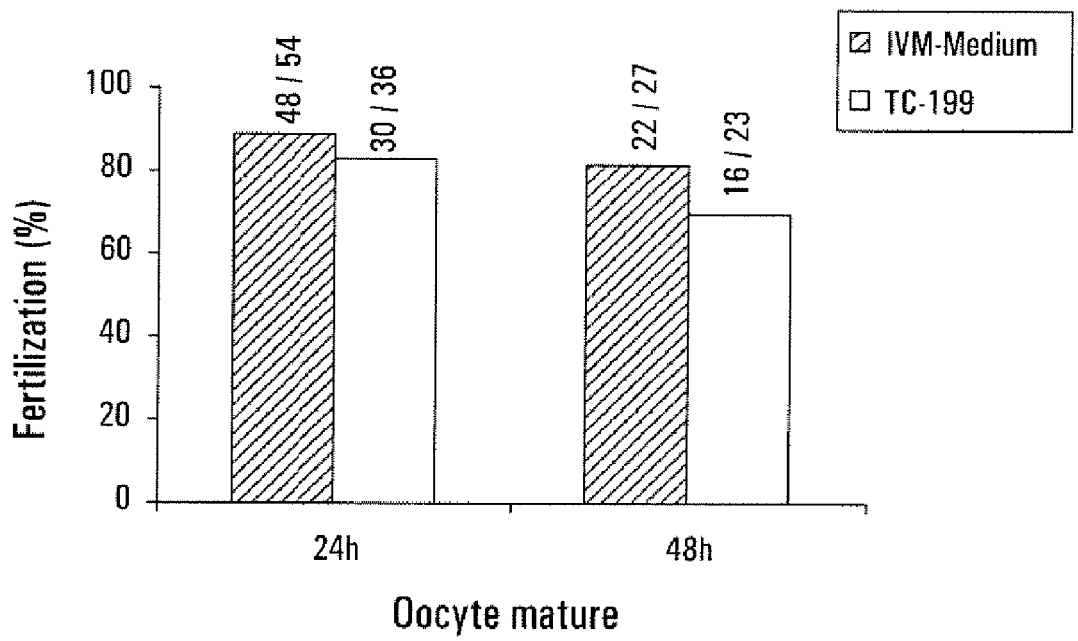
FIG. 4 shows fertilization rates of GV stage oocytes derived from stimulation and ICSI cycles following 24 h or 48 h of maturation.

There were also no differences in the fertilization rates between these two media when the oocytes were matured 24 h (88.9% vs. 83.3%) and 48 h (81.5% vs. 69.6%) (FIG. 4).

Figure 5:
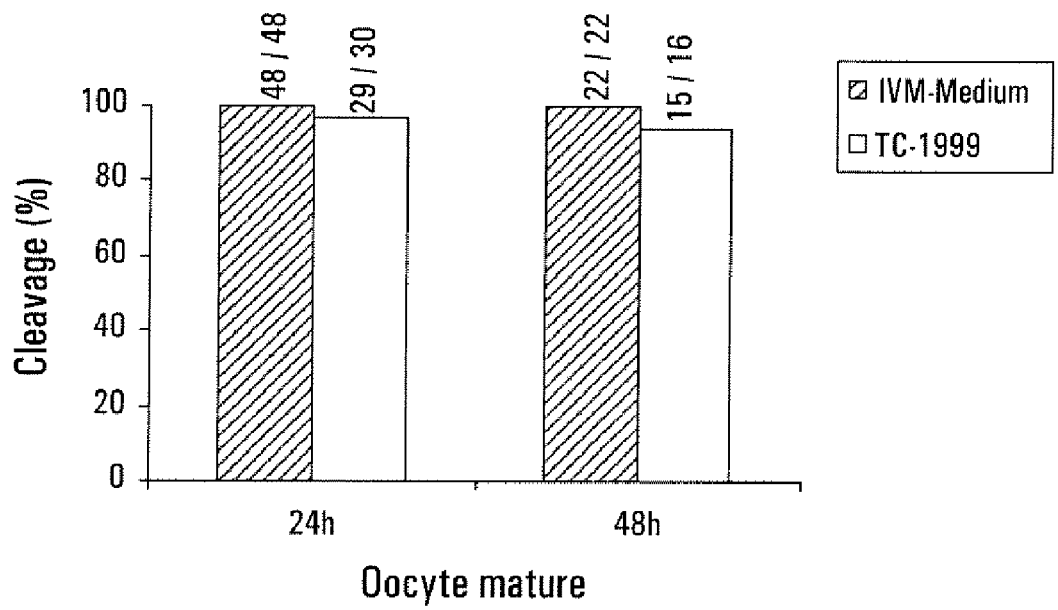
FIG. 5 shows cleavage rates of GV stage oocytes derived from stimulation and ICSI cycles following 24 h or 48 h of maturation.

Final cleavage rates were not different between these two media (Table 6, 100.0% vs. 95.6%). The cleavage rates of the fertilized oocytes were also not different between these two media when the oocytes matured 24 h (100.0% vs. 96.7%) and 48 h (100.0% vs. 93.8%) (FIG. 5).

However, there were significant differences (P<0.05) in embryos that developed to the 8-cell stage and blastocyst stage between the IVM-medium and TCM-199 (Table 6, 58.6% vs. 40.9% and 12.9% vs. 0.0%, respectively).

Figure 6A:
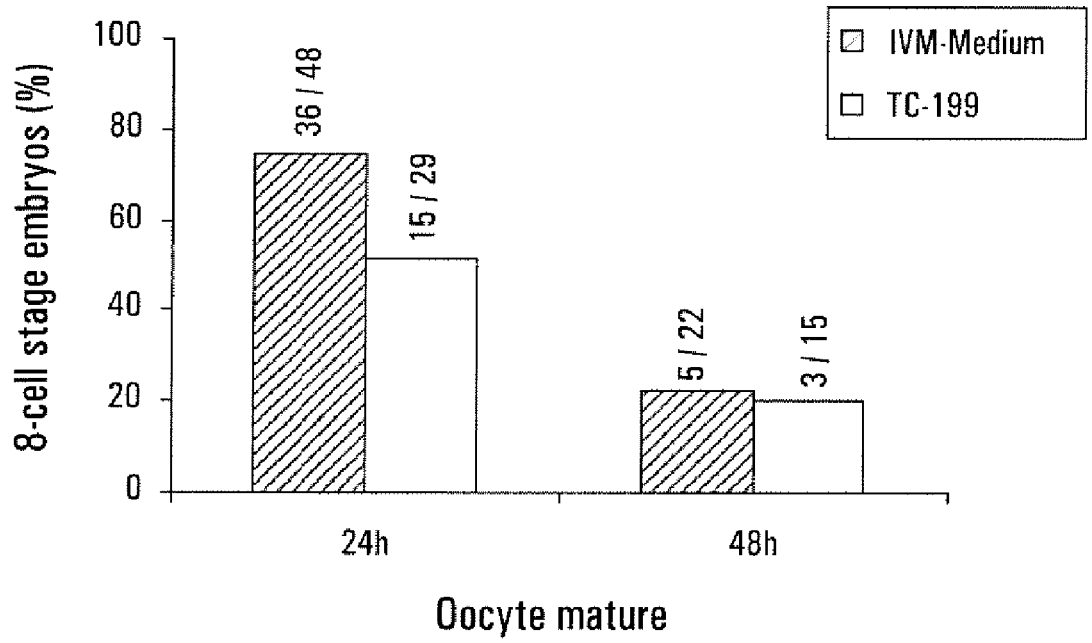
FIGS. 6A and 6B show embryos developing to the 8-cell stage (A) and the blastocyst stage (B) following 24 h or 48 h of maturation of GV stage oocytes derived from stimulation and ICSI cycles.
Figure 6B:
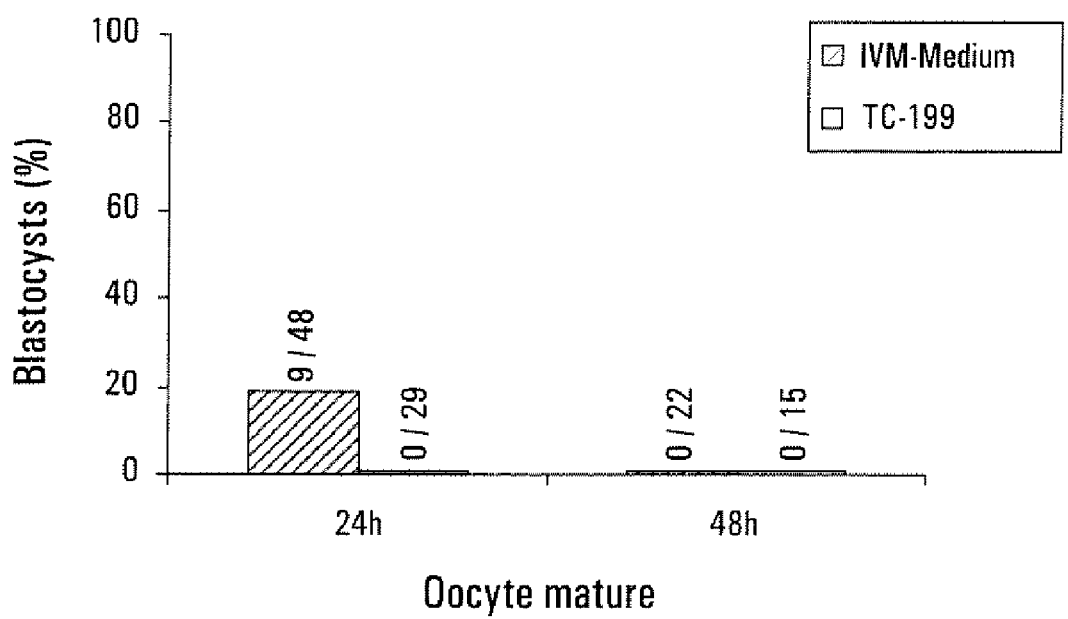
Figure 7:
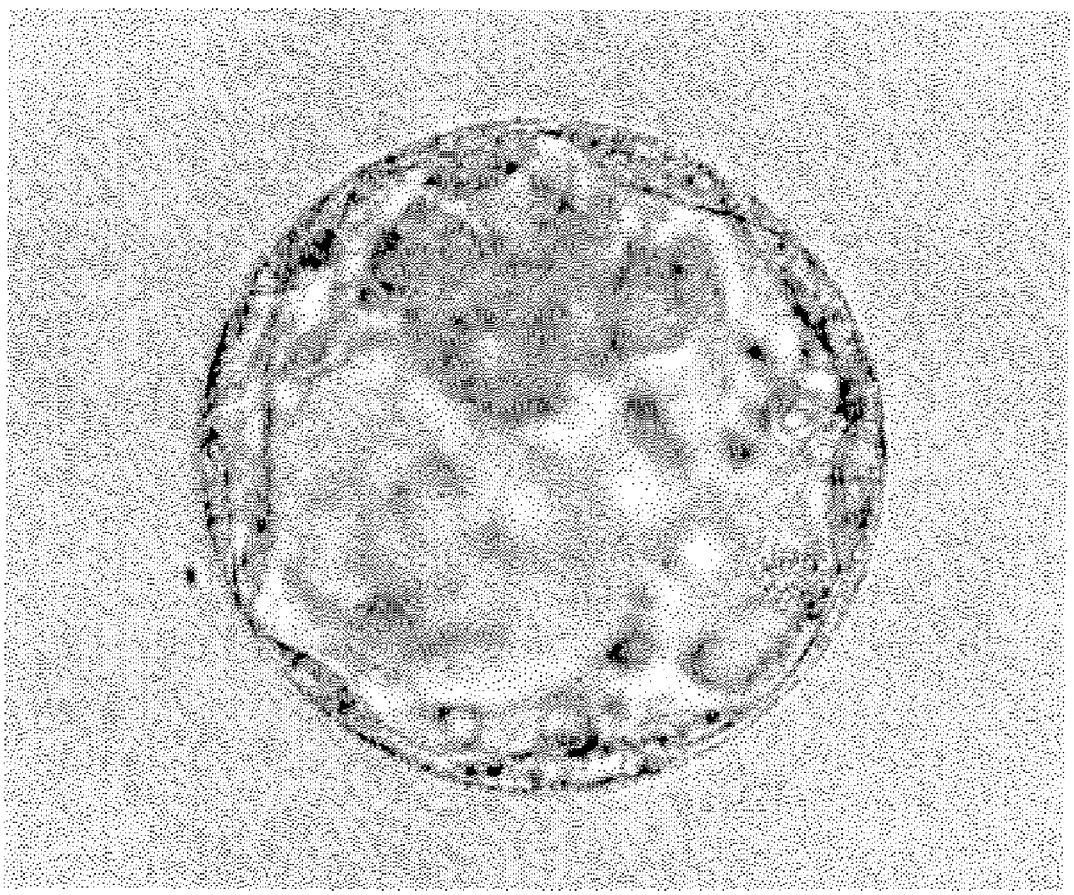
FIG. 7 shows a blastocyst derived from GV stage oocytes following 24 h of maturation in vitro and illustrates that there is no difference in morphology from oocytes matured in vivo. The scale bar indicates 5 µm length.

When oocytes were matured for 24 h, percentages of embryos that developed to the 8-cell stage (FIG. 6a; 75.0% vs. 51.7%) and the blastocyst stage (FIG. 6b; 18.8% vs. 0.0%) were significantly different (P<0.05) between the IVM-medium and TCM-199, respectively.

However, there were no differences in the embryos that developed to the 8-cell stage (FIG. 6a; 22.7% vs. 20.0%) and blastocyst (FIG. 6b; 0.0% vs. 0.0%) between these two media when the oocytes were matured for 48 h.

EXAMPLE 2

A total of 40 women with PCOS underwent 40 completed IVM treatment cycles. All patients were under 40 years of age (mean 32.3±3.9) and some patients presented irregular menstrual cycles or anovulation. All patients had a minimum 2-year history of infertility.

If the patients had irregular menstrual cycles, the treatment cycles was initiated by the administration of intra-vaginal progesterone (Prometrium; Schering, Pointe-Clair, Quebec, Canada) in a dose of 300 mg daily for 10 days. Withdrawal bleeding occurred within 3 days after the last dose.

On day 2 or 3 following the onset of menstrual bleeding, the patients underwent a baseline ultrasound scan to ensure that no ovarian cysts were present. Transvaginal ultrasound scans were repeated on day 8 to exclude the development of a dominant follicle. The size of all follicles on ultrasound scan had to be <10 mm in diameter on day 8 of the cycle.

Oocyte retrieval was performed on day 10 to 14 of the cycle. Before oocyte collection 36 hours, the patients were given s.c. 10,000 IU of human chorionic gonadotropin (HCG) for priming.

Transvaginal ultrasound-guided oocyte collection was performed using a specially designed 19 G single-lumen aspiration needle (Cook, Australia) with an aspiration pressure of 7.5 kPa. Aspiration of all small follicles was performed under local anaesthesia. Oocytes were collected in 10 ml culture tubes (Falcon, USA) containing 2.0 ml warm 0.9% saline contained with 2 IU/ml heparin (Baxter, Toronto, Ontario, Canada).

Following oocyte collection, cumulus-oocyte complexes (COCs) were cultured in an organ tissue culture dish (60×15 mm; Falcon) containing 1 ml of modified IVM-medium (Table 2) at 37° C. in an atmosphere of 5% $CO_2$ and 95% air with high humidity.

Following culture of 24 and 48 hours, the mature oocytes (metaphase-II stage) were inseminated by ICSI. Fertilization was assessed 18 h after ICSI for the appearance of two distinct pronuclei and two polar bodies. Embryo transfer was performed on day 2 or 3 after ICSI. Since the oocytes were inseminated either 24 or 48 hours following culture, the developmental stages of embryos were variable.

For the preparation of the endometrium, the patients were given estradiol (Estace; Roberts Pharmaceutical, Mississauga, Canada) depending on the endometrial thickness on the day of oocyte retrieval in divided doses, starting on the day of oocyte retrieval. If the endometrial thickness on the day of oocyte retrieval was <4 mm, a 10 mg dose was administered; if it was >6 mm, a 6 mg dose was given. Luteal support was provided by 400 mg intravaginal progesterone (Prometrium) twice daily for 16 days starting from the day after oocyte collection.

A total of 653 immature oocytes were collected from 40 women with PCOS who underwent IVM treatment. Following culture of 48 hours, 81.5% (532/653) of oocytes became mature. Following embryo transfer, 13 patients became pregnant (32.5%=13/40). Results are tabulated in Table 7.

TABLE 1

Composition of oocyte in vitro maturation (IVM) medium.

| | mg/L |
|---|---|
| Inorganic Salt: | |
| $CaCl_2$ | 200.0000 |
| KCl | 400.0000 |
| $MgSO_4$ | 98.0000 |
| NaCl | 6800.0000 |
| $NaHCO_3$ | 1250.0000 |
| $NaH_2PO_4 \cdot H_2O$ | 125.0000 |

TABLE 1-continued

Composition of oocyte in vitro maturation (IVM) medium.

| | mg/L |
|---|---|
| Amino Acids: | |
| L-Alanine | 8.9000 |
| L-Arginine | 126.4000 |
| L-Asparagine | 13.2000 |
| L-Aspartic Acid | 13.3000 |
| L-Cystine | 24.0000 |
| L-Glutamic Acid | 14.7000 |
| L-Glutamine | 292.0000 |
| Glycine | 7.5000 |
| L-Histidine-HCl·$H_2O$ | 42.0000 |
| L-Isoleucine | 52.4000 |
| L-Leucine | 52.4000 |
| L-Lysine-HCl | 72.5000 |
| L-Methionine | 15.1000 |
| L-Phenylalanine | 33.0000 |
| L-Proline | 11.5000 |
| L-Serine | 10.5000 |
| L-Threonine | 47.6000 |
| L-Tryptophan | 10.2000 |
| L-Tyrosine | 36.0000 |
| L-Valine | 46.8000 |
| Vitamins: | |
| Biotin | 0.0100 |
| D-Ca Pantothenate | 1.0000 |
| Choline Chloride | 1.0000 |
| Folic Acid | 1.0000 |
| i-Inositol | 2.0000 |
| Nicotinamide | 1.0000 |
| Pyridoxal·HCl | 1.0000 |
| Riboflavin | 0.1000 |
| Thiamine·HCl | 1.0000 |
| Other Components: | |
| D-Glucose | 1000.0000 |
| Sodium Pyruvate | 110.0000 |
| Insulin | 5.0000 |
| Human Transferrin | 50.0000 |
| Selenite | 0.0052 |
| Hydrocortisone | 0.0036 |
| FGF | 0.0005 |
| EGF | 0.0010 |
| Phenol Red | 5.0000 |
| Penicillin G | 50.0000 units |
| Streptomycin | 50.0000 units |
| FSH | 0.075 IU/ml |
| LH | 0.075 IU/ml |
| estradiol | 1.0 µg/ml |

TABLE 2

Modified Composition of oocyte in vitro maturation (IVM) medium.

| | mg/L |
|---|---|
| $CaCl_2$ | 200.0000 |
| Inorganic Salt: | |
| $CaCl_2$ | 200.0000 |
| KCl | 400.0000 |
| $MgSO_4$ | 98.0000 |
| NaCl | 6800.0000 |
| $NaHCO_3$ | 1250.0000 |
| $NaH_2PO_4 \cdot H_2O$ | 125.0000 |
| Amino Acids: | |
| L-Alanine | 8.9000 |
| L-Arginine | 126.4000 |
| L-Asparagine | 13.2000 |
| L-Aspartic Acid | 13.3000 |

TABLE 2-continued

| | mg/L |
|---|---|
| L-Cystine | 24.0000 |
| L-Glutamic Acid | 14.7000 |
| L-Glutamine | 292.0000 |
| Glycine | 7.5000 |
| L-Histidine•HCl•$H_2O$ | 42.0000 |
| L-Isoleucine | 52.4000 |
| L-Leucine | 52.4000 |
| L-Lysine-HCl | 72.5000 |
| L-Methionine | 15.1000 |
| L-Phenylalanine | 33.0000 |
| L-Proline | 11.5000 |
| L-Serine | 10.5000 |
| L-Threonine | 47.6000 |
| L-Tryptophan | 10.2000 |
| L-Tyrosine | 36.0000 |
| L-Valine | 46.8000 |
| Vitamins: | |
| D-Ca Pantothenate | 1.0000 |
| Choline Chloride | 1.0000 |
| Folic Acid | 1.0000 |
| i-Inositol | 2.0000 |
| Nicotinamide | 1.0000 |
| Pyridoxal•HCl | 1.0000 |
| Riboflavin | 0.1000 |
| Thiamine•HCl | 1.0000 |

TABLE 2-continued

| | mg/L |
|---|---|
| Other Components: | |
| D-Glucose | 1000.0000 |
| Sodium Pyruvate | 110.0000 |
| Estradiol | 1.0000 |
| Phenol Red | 5.0000 |
| FSH | 75.0000 IU |
| LH | 75.0000 IU |
| Human serum albumin | 1000.0000 |
| Penicillin G | 50.0000 units |
| Streptomycin | 50.0000 μg |

TABLE 3

Maturation of immature human oocytes (metaphase-I stage) cultured 6 h, 24 h or 48 h in the IVM-medium or TCM-199.

| Culture media | No. of oocytes examined | No. of oocytes matured at (%): 6 h | 24 h | 48 h |
|---|---|---|---|---|
| IVM medium | 154 | 80 (52.0) | 117 (76.0) | 121 (78.6) |
| TCM-199 | 154 | 71 (46.1) | 104 (67.5) | 109 (70.8) |

TABLE 4

Fertilization and embryonic development of immature human oocytes (metaphase-I stage) matured in the IVM-medium or TCM-199.

| Culture media | No. of oocytes inseminated | No. of oocytes fertilized (%) | No. of oocytes cleaved (%) | No. of embryos developed to (%): 8-cell stage | Blastocyst |
|---|---|---|---|---|---|
| IVM medium | 121 | 110 (90.0) | 107 (97.3) | 68 (63.6) | 21 (19.6)[a] |
| TCM-199 | 109 | 92 (84.4) | 91 (98.9) | 52 (57.1) | 7 (7.7)[b] |

[a,b]Different letters indicate significant differences within columns (P < 0.05).

TABLE 5

Maturation of immature human oocytes (germinal vesicle stage) cultured 24 h or 48 h in the IVM-medium or TCM-199.

| Culture media | No. of oocytes examined | No. of oocytes matured at 24 h (%) | No. of oocytes matured at 48 h (%) |
|---|---|---|---|
| IVM medium | 107 | 54 (50.1)[a] | 81 (75.7)[a] |
| TCM-199 | 106 | 36 (34.0)[b] | 59 (55.7)[b] |

[a,b]Different letters indicate significant differences within columns (P < 0.05).

TABLE 6

Fertilization and embryonic development of immature human oocytes (germinal vesicle stage) matured in the IVM-medium or TCM-199.

| Culture media | No. of oocytes inseminated | No. of oocytes fertilized (%) | No. of oocytes cleaved (%) | No. of embryos developed to (%): 8-cell stage | Blastocyst |
|---|---|---|---|---|---|
| IVM medium | 81 | 70 (86.4) | 70 (100.0) | 41 (58.6)[a] | 9 (12.9)[a] |
| TCM-199 | 59 | 46 (78.0) | 44 (95.6) | 18 (40.9)[b] | 0 (0.0)[b] |

[a,b]Different letters indicate significant differences within columns (P < 0.05).

TABLE 7

Results of in vitro maturation and fertilization of oocytes using modified IVM-medium followed by embryo transfer in women with polycystic ovaries (PCO) or polycystic overy syndrome (PCOS) (from January 2002 to September 2002 at McGill Reproductive Center).*

| | |
|---|---|
| Cycles | 40 |
| Age—yrs | 32.3 ± 3.9 |
| No. of oocytes collected | |
| Total | 653 |
| Mean | 15.9 ± 5.9 |
| No. of oocytes matured (%) | 532 (81.5) |
| No. of oocytes fertilized (%) | 336 (63.2) |
| No. of oocytes cleaved (%) | 329 (97.9) |
| No. of embryos transferred | |
| Total | 154 |
| Mean | 3.9 ± 0.6 |
| No. of clinical pregnancies (%) | 13 (32.5) |
| No. of implantation (%) | 17 (11.0) |

*Plus-minus values are mean ± SD.

REFERENCES

Adams J, Polson D, Frank S. Prevalence of polycystic ovaries in women with anovulation or idiopathic hirsutism. Br Med J 1986; 293:355-359.

Barnes F L, Crombie A, Gardner D K, Kausche A, Lacham-Kaplan O, Suikkari A A, Tiglias J, Wood C, Trounson A O. Blastocyst development and birth after in vitro maturation of human primary oocytes, intracytoplasmic sperm injection and assisted hatching. Hum Reprod 1995; 10:3243-3247.

Brackett B G, Zuelke K A. Analysis of factors involved in the in vitro production of bovine embryos. Theriogenology 1993; 39:43-64.

Cha K Y, Koo J J, Ko J J, Choi D H, Han S Y, Yoon T K. Pregnancy after in vitro fertilization of human follicular oocytes collected from nonstimulated cycles, their culture in vitro and their transfer in a donor oocyte program. Fertil Steril 1991; 55:109-113.

Cha K Y, Chian R C, Maturation in vitro of immature human oocytes for clinical use. Hum Reprod Update; 4:103-120.

Chian R C, Niwa K, Sirard M A. Effects of cumulus cells on male pronuclear formation and subsequent early development of bovine oocytes in vitro. Theriogenology 1994; 41:1499-1508.

Chian R C, Sirard M A. Effects of cumulus cells and follicle-stimulating hormone during in vitro maturation on parthenogenetic activation of bovine oocytes. Mol Reprod Dev 1995; 42:425-431.

Chian R C, Park S E, Park E H, Son W Y, Chung H M, Lim J G, Ko J J, Cha K Y. Molecular and structural characteristics between immature human oocytes retrieved from stimulated and unstimulated ovaries. Gormel V, Leung P C K (eds), In Vitro Fertilization and Assisted Reproduction; Monduzzi, Bologna, pp 315-319.

Chian R C, Buckett W M, Too L L, Tan S L. Pregnancies resulting from in vitro matured oocytes retrieved from patients with polycystic ovary syndrome after priming with human chorionic gonadotropin. Fertil Steril 1999; 72:639-642.

Chian R C, Gulekli B, Buckett W M, Tan S L. Priming with human chorionic gonadotropin before retrieval of immature oocytes in women with infertility due to the polycystic ovary syndrome. New Eng J Med 1999; 341:1624-1626.

Chian R C, Ao A, Clarke H J, Tulandi T, Tan S L. Production of steroids from human cumulus cells treated with different concentrations of gonadotropins during culture in vitro. Fertil Steril 1999; 71:61-66.

Chian R C, Buckett W M, Tulandi T, Tan S L. Prospective randomized study of human chorionic gonadotrophin priming before immature oocyte retrieval from unstimulated women with polycystic ovarian syndrome. Hum Reprod 2000; 15:165-170.

Chian R C, Gulekli B, Buckett W M, Tan S L. Pregnancy and delivery after cryopreservation of zygotes produced by in-vitro matured oocytes retrieved from a woman with polycystic ovarian syndrome. Hum Reprod 2001; 16:1700-1702.

Edirisinghe W R, Junk S M, Matson P L, Yovich J L. Birth from cryopreserved embryos following in vitro maturation of oocytes and intracytoplasmic sperm injection. Hum Reprod 1997; 12:1056-1058.

Goud P T, Goud A P, Qian C, Layerge H, Van der Elst J, De Sutter P, Dhont M. In-vitro maturation of human germinal vesicle stage oocytes: role of cumulus cells and epidermal growth factor in the culture medium. Hum Reprod 1998; 13:1638-1644.

Gross-Weege W, Theobald K, Konig W. Inhibition of histamine release from rat peritoneal mast cells by a factor from human serum: identification as transferring. Agents Actions 1986; 19:10-17.

Jaroudi K A, Hollanders J M G, Elnour A M, Roca G L, Atared A M, Coskun S. Embryo development and pregnancies from in vitro matured and fertilized human oocytes. Hum Reprod 1999; 14:1749-1751.

MacDougal M J, Tan S L, Balen A, et al. A controlled study comparing patients with and without polycystic ovaries undergoing in vitro fertilization. Hum Reprod 1993; 8:233-237.

Maruo T, Ladines-Llave C A, Samoto T, Matsuo H, Manalo A S, Ito H, Mochizuki M. Expression of epidermal growth factor and its receptor in the human ovary during follicular growth and regression. Endocrinology 1993; 132:924-931.

Moor R M, Trounson A O. Hormonal and follicular factors affecting maturation of sheep oocytes in vitro and their subsequent developmental capacity. J Reprod Fertil 1977; 49:101-109.

Nagy Z P, Cecile J, Liu J, Loccuifer A, Devroey P, Van Steirteghem A. Pregnancy and birth after intracytoplasmic sperm injection of in vitro matured germinal vesicle stage oocytes: case report. Fertil Steril 1996; 65:1047-1050.

Pincus G, Enzmann E V. The comparative behaviour of mammalian eggs in vivo and in vitro. 1. The activation of ovarian eggs. J Exp Med 1935; 62:665-675.

Shea B F, Baker R D, Latour J P. Human follicular oocytes and their maturation in vitro. Fertil Steril 1975; 26:1075-1082.

Steel R G D, Torrie J H. Principles and procedures of statistics: a biometrical approach. New York, McGraw-Hill, 1980; pp 172-194.

Trounson A, Wood C, Kausche A. In vitro maturation and fertilization and developmental competence of oocytes recovered from untreated polycystic ovarian patients. Fertil Steril 1994; 62:353-362.

Trounson A O, Anderiesz C, Jones G M, Kausche A, Lolatgis N, Wood C. Oocyte maturation. Hum Reprod 1998; 13:52-62.

Trounson A, Anderiesz C, Jones G. Maturation of human oocytes in vitro and their developmental competence. Reproduction 2001; 121:51-75.

All references cited in this specification are herein incorporated by reference as if each individual reference were specifically and individually indicated to be incorporated by reference. The citation of any reference is for its disclosure prior to the filing date and should not be construed as an admission that the present invention is not entitled to antedate such reference by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed:

1. A method for in vitro maturation of immature human oocytes, said method comprising: culturing an immature human oocyte in a chemically defined culture medium comprising at least one inorganic salt, essential amino acids or a source thereof, and an energy source, said culture medium being free of added growth factors, estradiol, and human chorionic gonadotropin; wherein said oocyte has a cumulus that is at least partially intact, or said oocyte is cultured in the presence of cumulus cells, or both.

2. The method according to claim 1, said chemically defined culture medium being free of insulin.

3. The method according to claim 1, said chemically defined culture medium being free of human transferrin.

4. The method according to claim 1, said chemically defined medium being free of selenite.

5. The method according to claim 1, said chemically defined medium being free of hydrocortisone.

6. The method according to claim 1, wherein said immature human oocyte comprises an M-I stage ooctye.

7. The method according to claim 1, wherein said immature human oocyte comprises a GV-stage oocyte.

8. The method according to claim 1, wherein said immature human oocyte is cultured until it reaches M-II.

9. The method according to claim 1, comprising culturing said oocyte in said culture medium for about 24 to about 48 hours.

10. The method according to claim 1, comprising removing said cumulus cells after the oocyte has been cultured for about 12 to about 24 hours.

11. The method according to claim 1, wherein said immature human oocyte has been retrieved from a female human subject after administration of human chorionic gonadotropin, and wherein said subject has not undergone an ovarian stimulation protocol prior to oocyte retrieval.

12. The method according to claim 11, wherein said human chorionic gonadotropin is administered to said subject about 32 to about 40 hours prior to oocyte retrieval.

13. The method according to claim 11, wherein said human chorionic gonadotropin is administered to said subject in an amount of about 5000 to about 20,000 IU.

14. The method according to claim 11, wherein said subject has not been treated with a gonadotrophin releasing hormone agonist, human menopausal gonadotrophin or follicle stimulating hormone.

* * * * *